United States Patent [19]

Klee

[11] 3,985,166

[45] Oct. 12, 1976

[54] HIGH-PRESSURE SAMPLE INJECTION FOR LIQUID CHROMATOGRAPHY

[76] Inventor: Richard E. Klee, 1499 Sierra Ave., Napa, Calif. 94558

[22] Filed: June 2, 1975

[21] Appl. No.: 582,969

[52] U.S. Cl. ........................... 141/346; 73/422 GC; 73/425.6; 141/386
[51] Int. Cl.² ..................... G01N 1/00; B65B 37/06
[58] Field of Search ...... 73/422 GC, 425.6, 425.4 P, 73/61.1 C; 141/67, 258, 346, 349, 386

[56] References Cited
UNITED STATES PATENTS

| | | | |
|---|---|---|---|
| 2,991,647 | 7/1961 | Harris | 73/422 GC |
| 3,321,977 | 5/1967 | Topham | 73/422 GC |
| 3,566,697 | 3/1971 | Vannus | 73/422 GC |
| 3,566,698 | 3/1971 | Sheppard | 73/422 GC |
| 3,583,230 | 6/1971 | Patterson | 73/422 GC |
| 3,656,351 | 4/1972 | Raczak | 73/425.6 |

Primary Examiner—S. Clement Swisher

[57] ABSTRACT

In a liquid chromatography apparatus, a stream of fluid flows at uninterruptedly high-pressure through a valve structure into a chromatographic column. The valve structure comprises an entrance port and a check valve through which a quantity of sample fluid can be introduced into the high-pressure carrier fluid stream. The entrance port of the valve structure is configured to mate in leak-tight sample fluid communication with an exit port on a high-pressure sample fluid delivery device. In a preferred embodiment, the high-pressure sample fluid delivery device is configured as a hand-gun, with a piston disposed in the barrel thereof to eject a quantity of sample fluid from the muzzle thereof. In this embodiment, the barrel of the gun is received within the entrance port of the valve structure so as to form a high-pressure seal.

9 Claims, 2 Drawing Figures

HIGH-PRESSURE SAMPLE INJECTION FOR LIQUID CHROMATOGRAPHY

BACKGROUND OF THE INVENTION

1. Field of the Invention

This is a further development in the field of liquid chromatography, and relates particularly to means for injecting a sample fluid into a high-pressure stream of carrier fluid.

2. Description of the Prior Art

In liquid chromatography, the sample fluid to be analyzed is often mixed with a carrier fluid of known composition for transport through a chromatographic column. In terms of minimizing the time required for analyzing a succession of samples, it is advantageous for the carrier fluid to flow at uninterruptedly high pressure into the chromatographic column. However, unless each quantity of sample fluid to be analyzed is introduced into the high-pressure carrier stream at a comparable high pressure, special sealing techniques must be devised to accommodate the pressure differential between the sample fluid and the stream of carrier fluid. Such special sealing techniques as have been developed to date are not completely reliable and frequently leak, thereby causing inaccuracy in the analysis. The alternative of providing for interruption of the high-pressure flow of the carrier fluid so as to permit introduction of a quantity of sample fluid at low pressure into the carrier stream is disadvantageous in terms of wear and tear on pump components and control elements. The preferable approach is to introduce the sample fluid into the high-pressure carrier stream at a comparable high pressure. An apparatus and method for accomplishing same is disclosed on copending patent application Ser. No. 493,593, filed Aug. 1, 1974, by Richard E. Klee and Joseph A. Varozza and assigned to Varian Associates.

SUMMARY OF THE INVENTION

The present invention provides a new apparatus and method for introducing a sample fluid at high pressure into a comparably high-pressure stream of carrier fluid for transport through an analysis instrument. Means are provided for causing the flow of a carrier fluid at uninterruptedly high pressure through a valve structure into a chromatographic column. The valve structure comprises an entrance port and a check valve through which a quantity of sample fluid can be introduced into the carrier fluid stream. The check valve is biased to remain closed so as to prevent entry of the sample fluid into the high-pressure carrier fluid stream, and obversely to prevent leakage of carrier fluid away from the valve structure through the sample fluid entrance port. The bias of the check valve can be overcome so as to admit sample fluid into the carrier fluid stream only when the pressure of the sample fluid against the check valve equals or exceeds the pressure of the carrier fluid stream. The sample fluid is delivered to the entrance port of the valve structure by a hand-operable delivery device which is configured to mate in leak-light sample fluid communication with the entrance port of the valve structure.

In a preferred embodiment, the sample fluid delivery device is configured as a hand-gun with a piston disposed in the barrel thereof to eject a quantity of sample fluid out through its muzzle. The entrance port of the valve structure is configured to receive the barrel of the gun-like sample fluid delivery device and to engage therewith in a fluid-tight coupling. According to a particular configuration, the gun barrel of the sample fluid delivery device is generally cylindrical in shape with a key structure projecting radially outward therefrom, and the mating entrance port of the valve structure is correspondingly cylindrical in shape with a keyway disposed therein to receive the key structure of the gun barrel when the gun barrel is fully inserted into the entrance port. Sealing means, comprising for example an O-ring, is provided at an interface between the sample fluid delivery device and the entrance port of the valve structure. When the gun barrel is fully inserted into the entrance port of the valve structure, the gun barrel can be twisted by, for example 90° thereby causing the key structure to travel in the keyway so as to lock the delivery device to the valve structure. Such locking of the sample fluid delivery device to the valve structure serves to compress the O-ring, thereby providing a leak-tight seal between the delivery means and the valve structure. Movement of the piston within the gun barrel serves to push a quantity of sample fluid against the check valve in the valve structure at sufficient pressure to overcome the bias of the check valve to remain closed. A quantity of sample fluid is thereby admitted past the check valve into the high-pressure carrier gas stream.

It is an object of this invention to provide a liquid chromatography apparatus capable of receiving injections of quantities of high-pressure sample fluid into a high-pressure stream of carrier fluid, where the sample fluid is delivered to the carrier fluid stream through a valve structure having an entrance port capable of mating in a fluid-tight connection with a hand-operable sample fluid delivery device.

It is a further object of this invention to use, in combination, a sample fluid delivery device configured as a hand-gun, and a valve structure providing an uninterrupted flow channel from a source of high-pressure carrier fluid to a chromatographic column, where the valve structure comprises entrance port means for receiving the barrel of the gun-like delivery device in leak-tight sample fluid communication therewith and check valve means for admitting a quantity of sample fluid to the high-pressure carrier fluid stream only when the pressure of the sample fluid equals or exceeds the pressure of the carrier fluid stream.

Other objects of this invention will become apparent upon a perusal of the following specification and accompanying drawing.

DESCRIPTION OF A PREFERRED EMBODIMENT

Figure 1:
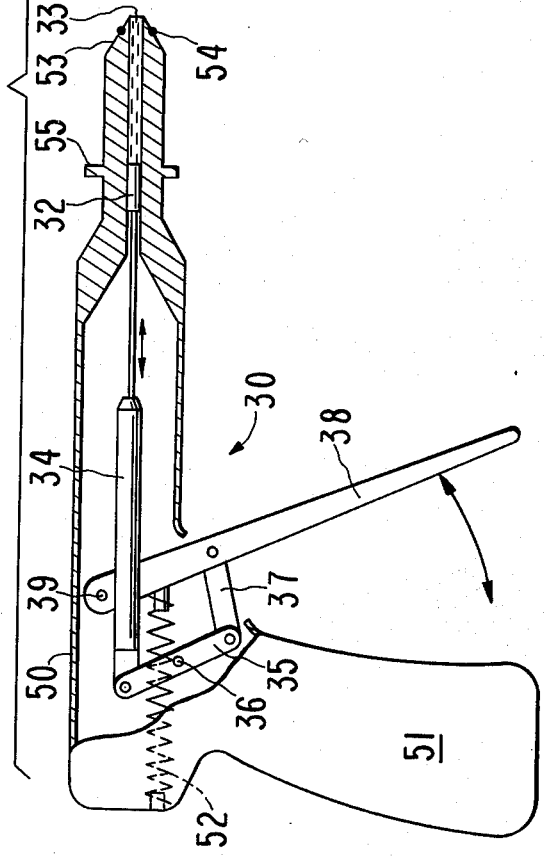
FIG. 1 illustrates in block form a liquid chromatography apparatus using this invention.

FIG. 1 shows a liquid chromatographic system comprising a carrier liquid source or reservoir 12 connected to a pump 14 for delivering a high-pressure stream of carrier liquid to an analysis column 16. The pump 14 typically is capable of delivering a carrier liquid stream to the column 16 at a pressure anywhere in the range from slightly above 0 up to 8500 psig. A valve structure 18 comprises a portion of the carrier liquid flow channel from the pump 14 to the column 16, and provides uninterrupted high-pressure flow therebetween.

A quantity of sample liquid to be analyzed can be introduced into the high-pressure carrier liquid stream through the valve structure 18, as will be discussed more fully hereinafter. The effluent from the column 16 consists of a mixture of carrier liquid, usually of known composition, and the sample liquid introduced through the valve structure 18. A detector 20 monitors variations in one or more of the properties of the effluent from the column 16 in order to derive information relating to the qualitative and/or quantitative analysis of the effluent, and consequently of the sample liquid. Optionally, a display apparatus 22 such as a strip chart recorder can be connected to the detector 20 for producing a permanent record of the variations in the detected properties of the effluent.

The valve structure 18 comprises a sample liquid entrance port 40, through which a quantity of sample liquid can be introduced into the high-pressure carrier liquid stream. The sample liquid is delivered to the entrance portion 40 by a hand-operable delivery device 30, which in the preferred embodiment shown is configured as a hand-gun. The barrel 31 of the gun-like sample liquid delivery device 30 is receivable within the entrance port 40 of the valve structure 18 so as to provide leak-tight sample liquid communication between the delivery device 30 and the valve structure 18.

Figure 2:
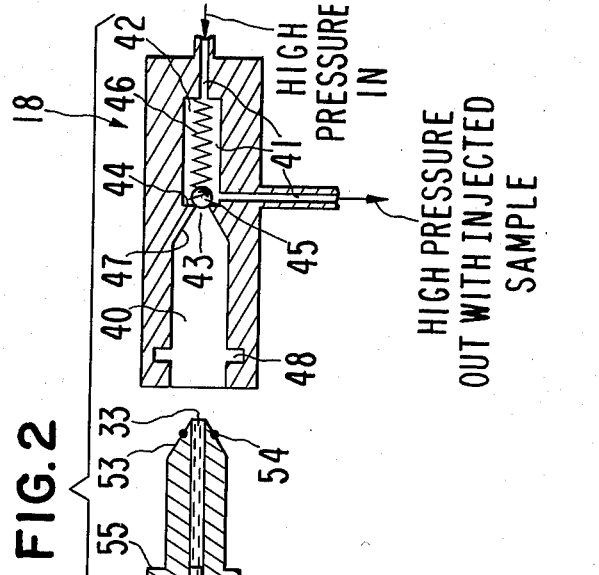
FIG. 2 illustrates a sample fluid delivery device and mating valve structure according to this invention.

The details of the valve structure 18 and the gun-like sample liquid delivery device 30 are shown in FIG. 2. The valve structure 18 comprises, in addition to the sample liquid entrance port 40, a wall structure 41 which defines a channel for uninterrupted flow of the carrier liquid from the pump 14 through a valve chamber 42 to the chromatographic column 16. An aperture 43 in the wall structure 41 of the valve chamber 42 provides communication between the sample liquid entrance port 40 and the flow channel of the carrier fluid. A portion of the wall structure 41 defining the periphery of the aperture 43 is configured as a checking-element seat 44. A checking element 45 is disposed within the valve chamber 42. The checking element 45 is configured to seat firmly in the seat 44 when the pressure of the carrier liquid in the valve chamber 42 is greater than the pressure of the sample liquid in the entrance port 40, thereby precluding communication between the entrance port 40 and the valve chamber 42. A spring 46 is provided to bias the checking element so as to remain firmly in the seat 44, thereby precluding communication between the entrance port 40 and the valve chamber 42 except when the pressure of the sample liquid in the entrance port 40 is equal to or greater than the pressure of the carrier liquid on the other side of the checking element 45 (i.e., within the valve chamber 42). The checking element 45 is typically a spherical ball, and the seat 44 is correspondingly a ball seal in the typical case.

The gun-like sample liquid delivery device 30 comprises a generally cylindrical barrel 31, within which is disposed a piston 32 for ejecting a quantity of sample liquid out of muzzle 33. The piston actuating mechanism disposed within the sample liquid delivery device 30 is conventional. In the embodiment shown in FIG. 2, the piston 32 is connected to a rod 34 which is hinged to one end of a rocket arm 35. The rocker arm 35 is pivotable about a fixed pivot 36 located at or near the midpoint thereof. The pivot 36 is affixed to the housing 50 of the gun-like delivery device 30. The other end of the rocker arm 35 is hinged to one end of a connecting arm 37. The other end of the connecting arm 37 is connected to a lever 38 at an intermediate point along the length thereof. One end of the lever 38 is pivotable about a pivot 39, which is affixed to the housing 50 of the gun-like delivery device 30. The other end of the lever 38 projects outwardly from the housing 50 in the manner of a trigger. It is desirable that the lever or trigger 38 be as long as is reasonably convenient, in order to provide as long a lever arm as possible. The housing 50 of the sample liquid delivery device 30 is configured to provide a hand grip portion 51, which is configured as a conventional piston grip. The trigger 38 may conveniently extend from the pivot 39 to a distance approximately coinciding with the bottom of the hand grip 51. A spring 52 has one end affixed to the housing 50, and the other end affixed to the trigger 38 at a point located between the pivot 39 and the point of attachment of the connecting arm 37. When the trigger 38 is squeezed (i.e., rotated about the pivot 39) toward the hand grip 51, the spring 52 becomes compressed. When the trigger 38 is released, the spring 52 expands so as to exert a torque on the trigger 38 which causes the trigger 38 to return to a normal position away from the hand grip 51.

The above-described components of the sample liquid delivery device 30 are configured with respect to each other such that an operator can conveniently hold his hand around the hand grip 51 and extend one or more of his fingers to curl around the trigger 38. As the trigger 38 is squeezed, the connecting arm 37 causes the rocker arm 35 to pivot about the pivot 36, thereby causing the rod 34 to translate toward the muzzle 33 of the gun barrel 31. Any liquid located in the gun barrel 31 between the piston 32 and the muzzle 33 would thereby be ejected from the delivery device 30 through the muzzle 33.

The gun-like sample liquid delivery device 30 can be loaded by squeezing the trigger 38 toward the handgrip 51, which causes the piston 32 to move forward toward the gun muzzle 33, and by then inserting the gun muzzle 33 into a container of sample liquid and subsequently releasing the trigger 38. Releasing the trigger 38 causes the piston 32 to withdraw rearward within the gun barrel 31. Atmospheric pressure on the surface of the sample liquid in the container then causes the sample liquid to follow the piston 32 up into the gun barrel 31. The loading action of the sample liquid delivery device 30 is similar to the loading process for a hypodermic syringe cylinder and piston.

A leak-tight mating of the gun barrel 31 with the sample liquid entrance port 40 of the valve structure 18 is accomplished by the matching geometrical configurations of the components, and by sealing means 54 disposed between the components when mating has occurred. In the embodiment shown in FIG. 2, the end 53 of the barrel 31 near the gun muzzle 33 is tapered, and a counterpart mating surface 47 is provided at the end of the cylindrical entrance port 40 near the aperture 43. The sealing means 54 is a resilient O-ring affixed to the tapered end 53 of the gun barrel 31. The O-ring seal 54 compresses so as to form a leak-tight seal between the surfaces 53 and 47 when the barrel 31 is fully inserted into the entrance port 40. Affixed to, or formed integrally with, the gun barrel 31 is a lug or key structure 55 extending radially outward therefrom. A counterpart keyway 48 is provided within the mating bore of the entrance port 40 to receive the lug or key 55. The key 55 and keyway 48 are configured with respect to each other so that when the gun barrel 31 is fully inserted into the entrance port 40, the gun barrel can be twisted by, say, a right-angle turn, thereby causing the key to travel in the keyway so as to lock the delivery device 30 to the valve structure 18. Such locking serves to retain the O-ring 54 in compression, thereby maintaining a leak-tight seal between the surfaces 53 and 47.

Forward movement of the piston 32 toward the gun muzzle 33 causes the sample liquid in the gun barrel 31 to bear against the checking element 45. A sample liquid pressure in excess of 10,000 psig can be exerted against the checking element 45 with very little exertion by the operator on the trigger 38. This high pressure can be easily and reliably obtained with the mechanical advantage provided by the trigger 38 and the linkage components 34, 35 and 37 on a relatively small-diameter piston 32. In a particular embodiment, a piston diameter of between 1/32-inch and 1/16-inch has been used. Such high pressure easily overcomes the bias of the checking element 43 to remain seated in the seat 44, and thereby allows the sample liquid to pass through the aperture 43 into the carrier liquid stream.

The preferred embodiment described above is intended to be illustrative of the invention. It is recognized, however, that particular changes in structural details may be made without departing from the scope of the invention, which is defined by the following claims or their legal equivalents.

What is claimed is:

1. Chromatography apparatus comprising a valve structure and a hand-operable sample-fluid delivery device; said valve structure comprising sample-fluid entrance port means, internal wall means defining a passageway for a stream of high-pressure carrier fluid from a carrier-fluid source to an analysis instrument, aperture means in said wall means to provide fluid communication between said sample-fluid entrance port means and said carrier-fluid passageway, and check-valve means being operable to admit sample fluid from said sample-fluid entrance port means into said carrier-fluid passageway only when the pressure of said sample fluid is at least as high as the pressure of the carrier-fluid in said passageway; and said sample fluid delivery device comprising exit port means configured to engage in leak-tight fluid communication with said sample-fluid entrance port means of said valve structure.

2. The apparatus of claim 1 wherein said aperture means is configured as a checking-element seat, and wherein said check-valve means comprises a checking element biased by a spring to remain in said seat except when the pressure of sample fluid delivered to said entrance port means is at least as high as the pressure of the carrier fluid in said passageway.

3. The apparatus of claim 2 wherein said checking element is a spherical ball.

4. The apparatus of claim 1 wherein said sample-fluid delivery device comprises a generally cylindrical exit port structure, and wherein said sample-fluid entrance port means of said valve structure is configured to receive said cylindrical exit port structure therewithin.

5. The apparatus of claim 4 wherein said cylindrical exit port structure has a tapered portion with a sealing ring affixed thereto, and wherein said sample-fluid entrance port means of said valve structure is configured to cause compression of said sealing ring when said exit port structure is inserted into said sample-fluid entrance port means.

6. The apparatus of claim 4 wherein said cylindrical exit port structure comprises key means projecting outwardly therefrom, and wherein said sample-fluid entrance port means comprises a keyway disposed to receive said key means when said exit port structure is inserted into said sample-fluid entrance port means.

7. The apparatus of claim 1 wherein said sample-fluid delivery device is configured as a hand-gun, the barrel thereof comprising said exit port means.

8. The apparatus of claim 7 wherein said hand-gun configured sample-fluid delivery device comprises piston means disposed within the barrel thereof, said piston means being operable to eject sample fluid from the muzzle thereof.

9. The apparatus of claim 8 wherein said piston means is operable by means of a trigger linked thereto via linkage arms.

* * * * *